United States Patent [19]

Pestka

[11] Patent Number: 4,623,621

[45] Date of Patent: Nov. 18, 1986

[54] IMMUNOASSAY FOR PEPTIDE AND PROTEIN OLIGOMERS

[75] Inventor: Sidney Pestka, North Caldwell, N.J.

[73] Assignee: Hoffmann-La Roche Inc., Nutley, N.J.

[21] Appl. No.: 653,167

[22] Filed: Sep. 24, 1984

Related U.S. Application Data

[63] Continuation of Ser. No. 391,628, Jun. 24, 1982, abandoned.

[51] Int. Cl.[4] ................ G01N 33/534; G01N 33/535; G01N 33/543
[52] U.S. Cl. .......................................... 435/7; 435/28; 436/518; 436/548; 436/804; 436/815; 935/110
[58] Field of Search ...................... 436/548, 518, 815; 435/7, 28; 935/110

[56] References Cited

U.S. PATENT DOCUMENTS 4,376,110  3/1983  David ................................. 436/548
4,514,507  4/1985  Secher ............................ 435/548 X

OTHER PUBLICATIONS

Secher, D. S. et al., Nature, 285, 446–450 (1980).
"Principles of Biochemistry" by A. White et al., Fourth Edition, pp. 147–148, McGraw-Hill, New York 1968.
Staehelin, T. et al., J. Biol. Chem., 256(18), 9750–9754 (1981).
Staehelin, T. et al., Proc. Natl. Acad. Sci. USA, 78 (3), 1848–1852 (1981).

*Primary Examiner*—Sidney Marantz
*Attorney, Agent, or Firm*—Jon S. Saxe; George M. Gould; Norman C. Dulak

[57] ABSTRACT

A convenient immunoassay for detecting the presence of oligomeric forms of peptides and proteins is described. The assay employs the sandwich technique with a monoclonal antibody selective for a single epitope on the peptide or protein bound to a solid phase and the same monoclonal antibody labeled with a detectable label in the solution phase.

7 Claims, No Drawings

IMMUNOASSAY FOR PEPTIDE AND PROTEIN OLIGOMERS

This is a continuation of application Ser. No. 391,628, filed June 24, 1982, now abandoned.

BACKGROUND OF THE INVENTION

The development of recombinant DNA technology has provided a source of producing large quantities of biologically and medically important peptides and proteins. These peptides and proteins are produced in host organisms and isolated from cell extracts under conditions and in concentrations quite different than the molecule would ordinarily see under the physiological conditions in which it naturally occurs. Such conditions can in certain instances favor the formation of dimer, trimer and higher oligomers of the peptide or protein molecule through intermolecular disulphide linkages, other covalent bonds, or non-covalent interactions.

Since in many cases these dimers and higher oligomers have either lower or no biological activity or else have the potential of causing deterious-side effects, such as antibody induction in patients, if the peptide or protein composition were to be used therapeutically by parenteral administration it is important to have available a selective assay which can distinguish these higher molecular species when present in admixture with the monomeric form. In this way it would be possible to carry out quality control analysis of the peptide or protein composition to detect the presence of the oligomers in the first instance and if present, would serve as a simple monitoring assay to assist in the purification of the compositions from the oligomers.

Immunoassays, particularly radio- or enzymeimmunoassays are well known in the art and have proved to be very useful for the detection and assay of peptides and proteins. Recently, monocloncal antibodies have become available. These antibodies have the property of being able to recognize a single epitope of a peptide or protein.

A sandwich-type immunoassay employing monoclonal antibodies that recognize different epitopes of the target protein has recently been developed for human leukocyte interferon, Staehelin et al., Methods Enzymol. 79, 589 (1981). In such assay one antibody is bound to a solid support in a manner which allows the antibody to bind any protein which has the specific epitope recognized by the antibody. A second monoclonal antibody that is labeled with a detectable label such as $^{125}I$ or peroxidase is used as a probe. The second monoclonal antibody has been raised against a second epitope on the protein and thus will bind to the protein which is already bound to the first monoclonal antibody.

Such a sandwich immunoassay cannot distinguish between the monomeric and the corresponding dimeric, trimeric and higher oligomeric forms of the protein because the second antibody will bind to each of these forms since they all will have the second epitope site available.

DESCRIPTION OF THE INVENTION

The present invention relates to a simple and convenient sandwich type immunoassay which is specific for oligomeric forms of a target peptide or protein. In the sandwich immunoassay of the present invention a monoclonal antibody which recognizes a single, select epitope on the target peptide or protein is coupled to a solid support in a manner known per se. Suitable solid supports for this purpose include, for example, plastic microtiter plates, such as most preferably polyvinylchloride plates. See for example Staehelin et al cited above.

The supported monoclonal antibody when contacted with the test solution containing the target protein will bind to all materials which contain the select epitope and thus will bind to monomeric, dimeric, trimeric and higher oligomeric forms of the target peptide or protein, if present.

In the second phase of the assay procedure of the invention, the monoclonal antibody coupled to the solid support is probed with the same monoclonal antibody which has been labeled with a detectable label. Any target monomeric peptide or protein which has been bound to the monoclonal antibody coupled to the solid phase will not have the epitopic binding site available since that site is already occupied. However, if the target peptide or protein is present in oligomeric forms then there are one or more free sites available to which the labeled monoclonal antibody can bind. Thus, the immunoassay will detect selectively any dimers or higher oligomers. Since the larger oligomers have more sites available than the smaller ones, more label should bind to the higher oligomers. In principle the number of sites available to the labeled antibody in an oligomer of n subunits is equal to n-1. In practice, however, it can be expected to be somewhat less because some of the oligomers may bind to the first antibody through more than one site.

Target peptides or proteins whose oligomeric forms can be selectively detected by means of the immunoassay of the present invention include the interferons, such as leukocyte, fibroblast and immune interferons, hybrid leukocyte interferons, growth hormone, insulin, lymphokines such as interleukin-1 and interleukin-2, serum albumin, somatostatin, chorionic gonadotropins, enzymes such as urokinase and the like. The aforesaid peptides and proteins can comprise human or other mammalian sequences such as ovine, porcine, murine, equine, feline, canine, bovine and the like. Such peptides or proteins can be naturally derived, synthetic or produced by recombinant DNA technology. They can be glycosylated or nonglycosylated.

An exemplary mode of the present invention is provided by the recombinant human leukocyte interferons, most particularly type IFL-rA.

Monoclonal antibodies which recognize specific epitopes on IFL-rA are known in the art. Descriptions of the preparation of such monoclonal antibodies are set forth by Staehelin et al. in Proc. Natl. Aca. Sci. U.S.A. 78, 1848 (1981); Staehelin et al. J. Biol. Chem. 256, 9750 (1981) and in U.S. patent application Ser. No. 351,282, filed Feb. 22, 1982, inventors Staehelin et al. Exemplary monoclonal antibodies which are described therein and which are useful in the practice of the present immunoassay for detection of oligomeric forms of IFL-rA include LI-1 and LI-9, with LI-1 being a preferred monoclonal antibody for this purpose.

The production of a monoclonal antibody to human leukocyte interferon has also been described by Secher et al., Nature 285, 446 (1980). Such a monoclonal antibody may also be employed in the practice of the present assay.

The labeled monoclonal antibody probe may utilize any convenient detectable label known in the immunoassay art which can be introduced without affecting the binding specificity of the antibody. Suitable labels include radiolabels such as $^3H$, $^{14}C$, $^{35}S$ and more preferably $^{125}I$ and $^{131}I$; enzyme labels such as horseradish peroxidase, fluorophores, chromophores, electron spin labels and the like. Preferred labels for practice of the present invention include the radiolabels, preferably $^{125}I$ and the enzyme labels, preferably horseradish peroxidase.

The present invention is further illustrated by the following examples.

EXAMPLE 1

Preparation of the monoclonal antibodies

(A) Interferon preparation

Partially purified human leucocyte interferon (IFL) was available in sufficient amount for the immunization of the mice. 5 IFL preparations are used:

(a) IFLγ(a) main peak of the fraction in accordance with U.S. Pat. No. 4,289,690 issued 9/15/81 with an approximate purity of 10–15% (estimated by sodium dodecyl sulphate-polyacrylamide gel electrophoresis) and specific activity in the antiviral test;

(b) IFL α; (c) IFL β;—(d) IFL γ; and (e) IFL δ.

The IFL a, β and γ fractions each consist of mixtures of the individual ($\alpha_1, \alpha_2$), ($\beta_1, \beta_2, \beta_3$) and ($\gamma_1, \gamma_2, \gamma_3, \gamma_4, \gamma_5$) species. These are shoulder fractions of the corresponding purified species which are pooled from different preparations. The IFL δ fraction is the shoulder of the δ-species. Besides the species a, β and γ on the Lichosorb-diol column there is occasionally seen a δ-fraction. This is purified as in step 9 in accordance with U.S. Pat. No. 4,289,690, it being evident that species δ shows no sub-species and is uniform. The purity of (b), (c) and (d) is between 20 and 40% in accordance with specific biological activity and in accordance with sodium dodecyl sulphate-polyacrylamide gel electrophoresis. The purity of (e) is at most 5%.

DETERMINATION OF INTERFERON ACTIVITY

The interferon activity is determined by means of the "cytopathic-effect-inhibition" (CPE) test in accordance with U.S. Pat. No. 4,241,174 (Ser. No. 963,256).

(B) Immunization of the mice 3 eight weeks old Balb c/J female mice are firstly immunized with IFLγ(a) in Freund's complete adjuvant. Each mouse receives approximately 150 μg total protein containing 20–25 μg of interferon in 0.25 ml at 5 different positions (0.05 ml in each position): subcutaneously in the left and right iliac region and in the left and right axilliary region as well as an intraperitoneal injection.

53 days later a second immunization is carried out as follows: interferon IFLγ(a) is separated by preparative sodium dodecyl sulphate-polyacrylamide (15%) gel electrophoresis in three 0.6×11 cm cylindrical gels. Approximately 300 μg total protein in 0.3 ml (dialyzed against sample buffer) containing approximately 40–50 μg of interferon are loaded per gel. [This procedure is carried out essentially according to the method of Laemmli, U.K. (1970) Nature 227, 680–685]. After electrophoresis, the gels are sliced into 2 mm thick discs. These are immersed for 10 minutes in 0.5 ml of phosphate-buffered sodium chloride solution (0.01M potassium phosphate buffer, pH 7.3; 0.14M sodium chloride) containing 0.1% Triton X-100 in polypropylene test tubes. The buffer is tested for interferon activity in serial dilution according to the CPE inhibition test. The discs 6 and 7 (numbered from the lower end of each gel) show the highest interferon activity (in each case approximately 25% of the activity of the total gel). Each disc with highest activity is finely sliced with a razor blade on a glass plate, transferred into a 1 ml syringe containing 0.2 ml of 0.15M sodium chloride and injected into each mouse. The gel suspension is injected intraperitoneally, wherein 0.2 ml of BCG (Bacillus Calmette-Guérin; Serum Institute Berne) is injected.

After 12 days, the serum of each mouse is tested for interferon neutralization activity. The serum of mouse No. 3 shows a 50% neutralization of 10 units/ml of IFLγ(a) at a dilution of 1:72 000, but does not neutralize the same concentration of crude IFL (<0.1% purity) even at a dilution of 1:100. The mice No. 1 and No. 2 show neutralization titres of less than 1:1000 against IFLγ(a).

70 days after the second immunization mouse No. 3 receives on three successive days an intraperitoneal booster injection with a mixture of IFL α, β and γ containing approximately 50 μg of interferon and 15 μl of normal mouse serum as the carrier protein (in 0.2 ml of 0.15M sodium chloride). 48 hours after the last injection the mouse is killed and the spleen is removed in order to prepare hybridomas.

(C) Cell cultures and cell fusions

The following materials and media are used. Iscove's modification of Dulbecco's modified Eagle medium (IMDMEM) is obtainable from Gibco. It is made up freshly with sodium pyruvate (1 mM), glutamine (1.5 mM), 2-mercaptoethanol ($5 \times 10^{-5}$M), penicillin (100 units/ml) and streptomycin (100 μg/ml). Complete HAT medium consists of thus-completed IMDMEM as well as hypoxanthine ($10^{-4}$M), aminopterin ($4 \times 10^{-7}$M), thymidine ($1.5 \times 10^{-5}$M) and 15% fetal calf serum. A 50% (w/v) solution of polyethyleneglycol 4000 (PEG 4000, Merck) in IMDMEM is prepared.

The fusion with a non-producing azaguanine-resistant myeloma cell line is carried out, with small modifications, according to the method of Stähli et al., J. Immunol. Methods 32, 297–304. In this fusion $48 \times 10^6$ nucleated spleen cells are fused with $25 \times 10^6$ myeloma cells of the line FO[(Fazekas de St. Groth and Scheidegger, J. Immunol. Methods 35, 1–25 (1980)]. The spleen cells and myeloma cells are washed in serum-free IMDMEM. They are then resuspended in the same medium, mixed in the aforementioned ratio for the fusion and sedimented in 40 ml of serum-free IMDMEM in a 50 ml conical polypropylene test tube at 200×g for 15 minutes, following which the supernatant is sucked off completely. To the cell sediment there are added dropwise while stirring constantly 0.5 ml of 50% PEG 4000 in order to resuspend and to disperse the cells. After approximately 90 seconds, 10 ml of serum-free IMDMEM are added dropwise during 4–5 minutes at room temperature while stirring constantly. After a further 15 minutes without stirring, large cell clumps are separated by cautious pipetting with a 10 ml pipette. The fusion mixing is diluted to 250 ml with complete HAT medium and then placed in 240 "Costar cluster wells (1 ml/well)" which already contain 1 ml of complete HAT medium and $10^5$ peritoneal mouse cells as the nutritive layer. The cultures are incubated in a 5% carbon dioxide/95% air atmosphere at 85% humidity. The cultures are fed twice a week by replacing half of the medium (1 ml) with fresh HAT medium.

(D) Detection of interferon-specific hydridomas by a solid phase-antibody binding test (SABA)

This method is adapted from the principle described by Catt and Tregear [Science 158, 1570–1572 (1967)] and is suitable for the detection of hybridoma antibodies [see also Stähli et al., J. Immunol. Methods 32, 297–304 (1980) as well as Kennet, R. H. in Current Topics in Microbiology and Immunology, Vol. 81, p. 77–91 (1978)]. Interferon preparations of IFL $\alpha$, $\beta$, $\gamma$ and $\delta$ are individually diluted in polypropylene test tubes with phosphate-buffered sodium chloride solution (PBS) to a final concentration of approximately 0.2 to 0.5 $\mu$g interferon/ml (approximately 1–3 $\mu$g total protein per ml; except for IFL $\delta$ where approximately 10–15 $\mu$g of total protein are present per ml) in order to coat therewith polyvinyl chloride microtitre plates (Cooke Laboratory products Division, Dynatech Laboratories, Inc.) as in the case of Stahli et al. 50 ul of the interferon solution is placed in each well and left for at least four hours at room temperature in a humid chamber or held at 4° C. up to several weeks. Before use the wells are filled with 3% bovine serum albumin (BSA) in PBS and left for 30 to 60 minutes in order to block all protein binding positions. The plates are then washed four times with PBS. 50 $\mu$l of supernatant of the hybridoma cultures are incubated in each of two wells for at least 4 hours at room temperature. Control experiments (unspecific binding) are carried out on plates which are coated only with 3% BSA. After washing four times with PBS, there are added to each well 50 $\mu$l of sheep-anti-mouse Ig-antibody (purified by affinity chromatography and labelled with $^{125}$I; 50 000 to 100 000 cpm per 20 to 30 ng of antibody in PBS containing 1% BSA) and incubation is carried out at room temperature for at least 4 hours. The plates are washed four times to five times with PBS and the divided into the individual wells, which are then tested for radioactivity in a gamma-scintillation spectrometer.

(E) Results (a) Initial screening by antibody binding (SABA) against partially purified IFL fractions 152 of the 240 cultures show growth of hybridomas. The supernatants are tested for interferon-specific antibodies in the SABA test, when the cultures are approximately 20–30% confluent (12–29 days after the fusion). Antibody binding is tested in parallel with IFL $\alpha$, IFL $\beta$, IFL $\gamma$ and IFL $\delta$. Of the 152 cultures, 13 supernatants show high antibody binding against all four partially purified interferon preparations. The medium of four further hybridomas shows lower binding activity (3–4 times greater than unspecific binding) against all four interferon preparations. These cultures are discarded. The media of all other hybridomas (135 growing cultures) yield unspecific bindings against all four IFL preparations. Of the 13 specific hybridomas, 9 are characterized as representative for the present invention. Their designation is LI-1, LI-2, LI-3, LI-5, LI-6, LI-7, LI-8, LI-9 and LI-12.

The antibody binding of the 9 specific hybridomas shows a different behaviour to the 4 partially purified interferon preparations. LI-1, LI-2, LI-3, LI-5, LI-6, LI-7 and LI-8 show an identical characterization with the following binding sequence: IFL $\alpha <$ IFL $\delta <$ IFL $\gamma <$ IFL $\beta$. For LI-9 the binding order is IFL $\delta <$ IFL $\gamma <$ IFL $\beta$. LI-12 is different from all others.

(b) Antibody binding (SABA) against highly purified leucocyte interferon

Six purified ($\geq$80% pure) interferon species are immobilized by adsorption on polyvinyl chloride microtitre plates. These species are IFL $\alpha_1$, $\alpha_2$, $\beta_2$, $\gamma_2$ and $\gamma_3$ as well as IFL-K of the cell line KG-1 [Koeffler, H. P. et al., Science 200, 1153–1154 (1978)] which is purified in analogy to steps 1 to 9 of Table 3 of the aforementioned DOS. Since no clear separation into individual species was observed in steps 8 and 9 of this preparation (IFL-K), the main fraction with the interferon activity was pooled. It is accordingly a mixture of different species. The adsorption of interferon (50 $\mu$l/per well) is carried out overnight with approximately 0.5 $\mu$g of interferon and 2 $\mu$g of BSA per ml of PBS followed by the blocking of the protein binding positions with 3% BSA as described previously.

The antibody binding with the culture medium of the 9 specific hybridomas against the 6 different, purified interferons was tested. Various groups of antibodies with different characteristic binding behaviour can again be differentiated. Group 1 embraces the antibodies LI-1 and LI-2 which have identical binding characteristics, but which do no recognize IFL $\gamma_3$. Group 2 embraces the antibodies LI-3, LI-5, LI-6, LI-7 and LI-8 with a possible differentiation of two sub-groups. Sub-group 2a (LI-3, LI-5 and LI-6) shows overall higher binding than sub-group 2b (LI-7 and LI-8), the latter sub-group binding relatively stronger to purified IFL $\alpha_1$ and IFL-K than the first. According to the interferon binding behaviour of the remaining antibodies, LI-9 has the most characteristics of sub-group 2b. LI-12 appears, in turn, to be unique.

Because of the high antibody binding to different purified interferons it is very unlikely that any of these antibodies was directed against contaminants. This is indicated for most of these antibodies also by the capability of neutralizing the biological activity of interferon. LI-1, LI-2, LI-3, LI-5, LI-6, LI-7, LI-8 and LI-9 annul the inhibition of the viral CPE on MDBK cells induced by interferon. The interferon neutralization is tested with partially purified IFL$\gamma$(a) and/or purified IFL-K, IFL $\gamma_1$, IFL $\alpha_2$ and crude leucocyte interferon. None of the antibodies was capable of neutralizing crude leucocyte interferon. LI-12 neutralized none of the tested interferons. The capability of the antibodies in accordance with the invention to bind interferons obtained by recombinant DNA technology was observed.

(2) Isotypes of the heavy and light chains of the monoclonal interferon antibodies Monoclonal antibodies of hybridoma culture medium are firstly bound to interferon-coated microtitre plates as has been described previously for the SABA test. After washing, they are incubated with isotype-specific rabbit anti-mouse Ig antiserum (Nordic). Goat anti-rabbit IgG which is labelled with horseradish-peroxidase is used for the detection. The enzyme substrates used are 2,2'-azino-di-(3-ethyl-benzothiazoline sulphate) and hydrogen peroxide.

Seven of the tested antibodies have the immunoglobulin chains $\gamma_1$/k, one has $\gamma_{2b}$/k and one has $\mu$/k. All seven $\gamma_1$/k antibodies as well as the $\gamma_{2b}$/k neutralize interferon, whereas the $\mu$/k does not neutralize interferon.

(3) Cloning and stabilization of the interferon-specific hybridomas

In order to prepare stable hybridoma lines, all 9 specific hybridomas are cloned by limiting dilution in microtitre plates with mouse-peritoneal cells as the nutritive layer [Hengartner H. et al., Current Topics in Microbiology and Immunology, Vol. 81, 92-99 (1978)]. The cloning was begun when the original cultures were transferred into flasks or shortly thereafter. The clones were tested against IFL β using the SABA test.

From each hybridoma there are intensively cultivated two to four strongly positive clones and these are not only injected intraperitoneally into mice for ascites production but also frozen. In most cases the selected clones of a hybridoma are pooled for simplification and reduction of work. From all 9 hybridomas there is obtained ascites liquor for the production of antibodies on a large scale. Ascites cells are likewise transferred into cultures and frozen.

(4) Grouping of the antibodies according to their interactions with purified leukocyteinterferon species The main group of the seven hybridomas, which produce $\gamma_1/k$ immunoglobulin, can be divided into two groups on the basis of their antibody interaction with purified interferons. The first group (LI-1 and LI-2) does not recognize purified IFL $\gamma_3$, whereas the second group (LI-3 and LI-5 to LI-8) recognizes IFL $\gamma_3$. The relative, quantitative binding of the monoclonal antibodies to six different purified interferons and the difference between neutralizing and non-neutralizing antibodies yields information for the differentiation of different epitopes (antigenic determinants) of the interferon species and for the demonstration of structural differences between different purified interferons. From the binding behaviour of the antibodies it is clear that LI-1 and LI-2 recognize a different structure than all other antibodies and that IFL $\gamma_3$ is structurally different from all other tested interferons, since it does not exhibit the epitope recognized by LI-1 and LI-2. LI-12, a non-neutralizing antibody, recognizes with approximately the same, although perhaps lower, affinity a less variable determinant which is present in all tested interferons. The results of the antibody binding and of the interferon neutralization indicate that at least three different epitopes of the leukocyte interferons can be recognized and defined by the collection of the monoclonal antibodies.

EXAMPLE 2

Human Leukocyte Interferon—Sandwich RIA

Each well of a PVC-microtiter plate is coated with 100 μl of LI-1 (10 μg/ml in PBS) at room temperature overnight or at 4° C. for several days or weeks in a humid chamber. Before use, the solution of LI-1 is removed and the wells are filled with Solution I [phosphate-buffered saline (PBS) containing 10% fetal calf serum and 160 μg/ml human IgG] for at least 15 minutes and then washed four times with the aforesaid PBS solution. A total of 100 μl per well of interferon test solution in PBS containing 1 mg/ml of bovine serum albumin (BSA) is added and incubated at room temperature for two hours. The solution is removed and 100 μl of [$^{125}$I]LI-1 (approximately 200,000/50 ng) in Solution I are added to each well. The plates are held at room temperature for two hours and then washed four times with PBS. Radioactivity in the individual wells is determined with a gamma scintillation spectrometer. The results obtained with solutions containing known concentrations of monomeric, dimeric and higher oligomeric forms of IFLrA are set forth in following Table I. Standard curves derived from such results can be used to determine the concentration of oligomers in unknown test solutions.

TABLE I

| Interferon (IFLrA) Concentration (ng/ml) | COUNTS/MIN OF [$^{125}$I]LI-1 BOUND | | |
|---|---|---|---|
|  | Monomer | Dimer | Trimer |
| 0 | 0 | 0 | 0 |
| 3 | 14 | 21 | 40 |
| 10 | 26 | 102 | 254 |
| 30 | 74 | 754 | 1,439 |
| 100 | 281 | 5,182 | 7,239 |
| 300 | 380 | 8,742 | 17,907 |

EXAMPLE 3

Enzyme-Linked Immunosorbent Assay for Oligomers of IFLrA

Standard solutions of IFLrA oligomers are diluted to 20, 50, 100, and 200 ng/ml with 0.1M sodium phosphate, pH 6.5, containing 2.5 mg/ml of bovine serum albumin. Unknowns to be tested are not diluted. Aliquots (0.05 ml) of standard solutions and unknowns are transferred into wells of a 96-well microtiter culture plate coated with monoclonal antibody LI-1 followed by 0.05 ml monoclonal LI-1 conjugated with horseradish peroxidase. The plate is then incubated in the dark at 25° C. for 2 hours. The liquid contents of the wells are discarded and the wells of the plate are washed five times with phosphate-buffered saline. Substrate solution consisting of o-phenylene-diamine (20 mM) in 0.1M potassium citrate, pH 5.5, with 5 mM $H_2O_2$ is prepared and 0.10 ml is added to each well. The plate is then incubated in the dark for 30 minutes at 25° C. The color reaction is stopped by the addition of 4N HCl containing 2 mg/ml of ascorbic acid. The optical density at 488 nm is measured photometrically and recorded. The values obtained using standard concentrations of monomeric and oligomeric IFLrA are indicated in the following Table II. This assay is a one-step assay where both interferon oligomers and monoclonal antibody LI-1 conjugated with peroxidase are incubated together. In this case, excess interferon oligomers reduces the amount of peroxidase-conjugated LI-1 bound in a biphasic manner (see Staehlin et al., *Methods Enzymol.* 79, 589-595 [1981]). This assay can be carried out by incubating interferon and the second antibody sequentially as described in Example 1.

TABLE II

| Interferon (IFLrA) Concentration (ng/ml) | PEROXIDASE-CONJUGATED LI-1 BOUND (OPTICAL DENSITY AT 488 NM) | | |
|---|---|---|---|
|  | Monomer | Dimer | Trimer |
| 0 | 0 | 0 | 0 |
| 20 | 0.002 ± 0.0005 | 0.044 ± 0.02 | 0.092 ± 0.04 |
| 50 | −0.0017 ± 0.007 | 0.095 ± 0.02 | 0.160 ± 0.04 |
| 100 | 0.0073 ± 0.006 | 0.127 ± 0.02 | 0.242 ± 0.07 |
| 200 | 0.003 ± 0.01 | 0.065 ± 0.01 | 0.138 ± 0.02 |

I claim:

1. A method for the assay of oligomeric forms of a peptide or protein which comprises contacting a test solution with a monoclonal antibody coupled to a solid support, said monoclonal antibody being capable of binding specifically to an epitopic site which is present only once on said peptide or protein, whereby any monomeric or oligomeric form of said peptide or protein present in said test solution is bound to said solid supported monoclonal antibody; thereafter contacting said solid supported monoclonal antibody with a solution containing the same monoclonal antibody bearing a detectable label whereby said labeled monoclonal antibody will selectively bind to any oligomeric form of said peptide or protein bound to the solid supported monoclonal antibody; and measuring the amount of labeled monoclonal antibody bound to the solid support, which amount will be proportional to the amount of oligomeric form of said peptide or protein present in said test solution.

2. The method of claim 1 wherein said protein is an interferon.

3. The method of claim 2 wherein said interferon is a recombinant human leukocyte interferon.

4. The method of claim 3 wherein said recombinant human leukocyte interferon is IFL-rA.

5. The method of claim 4 wherein said monoclonal antibody is specific for human leucocyte.

6. The method of claim 5 wherein said labeled monoclonal antibody is $^{125}$I labeled.

7. The method of claim 5 wherein said labeled monoclonal antibody is conjugated to peroxidase.

* * * * *